(12) United States Patent
Harvey et al.

(10) Patent No.: US 11,918,790 B2
(45) Date of Patent: Mar. 5, 2024

(54) DRUG INJECTION DEVICE

(71) Applicant: Stevanato Group S.p.A., Piombino Dese (IT)

(72) Inventors: Oliver Taylor Harvey, Ickleton (GB); Christopher John Hurlstone, Ickleton (GB); Isobel Rachel Sands, Ickleton (GB); Rhona Ann Sinclair, Ickleton (GB)

(73) Assignee: Stevanato Group S.P.A., Piombino Dese (IT)

( * ) Notice: Subject to any disclaimer, the term of this patent is extended or adjusted under 35 U.S.C. 154(b) by 0 days.

(21) Appl. No.: 18/069,909

(22) Filed: Dec. 21, 2022

(65) Prior Publication Data
US 2023/0201469 A1 Jun. 29, 2023

(30) Foreign Application Priority Data
Dec. 23, 2021 (IT) .................. 102021000032357

(51) Int. Cl.
*A61M 5/315* (2006.01)
(52) U.S. Cl.
CPC ...... *A61M 5/3155* (2013.01); *A61M 5/31541* (2013.01); *A61M 5/31578* (2013.01)
(58) Field of Classification Search
CPC ............ A61M 5/3155; A61M 5/31541; A61M 5/31578
See application file for complete search history.

(56) References Cited

U.S. PATENT DOCUMENTS

| | | | |
|---|---|---|---|
| 8,512,296 B2 | 8/2013 | Gabriel et al. | |
| 9,352,098 B2 | 5/2016 | Veasey et al. | |
| 10,569,024 B2 | 2/2020 | Harms et al. | |
| 2016/0082196 A1* | 3/2016 | Higgins | A61M 5/31536 604/211 |
| 2019/0358407 A1* | 11/2019 | Hewson | A61M 5/31585 |
| 2019/0366007 A1 | 12/2019 | Hewson et al. | |

FOREIGN PATENT DOCUMENTS

| | | |
|---|---|---|
| DE | 202012001411 U1 | 7/2013 |
| EP | 3603703 A1 | 2/2020 |
| WO | 2014166919 A1 | 10/2014 |
| WO | 2015181141 A1 | 12/2015 |

\* cited by examiner

*Primary Examiner* — Dung T Ulsh
(74) *Attorney, Agent, or Firm* — Husch Blackwell LLP

(57) ABSTRACT

A drug injection device includes a last dose setting having a main drive pin, a drive wheel, a driven wheel, an abutment element fixedly coupled to, or integrally formed with, the driven wheel. The drive wheel has a rotation axis parallel to a longitudinal axis and is configured to be driven about the longitudinal axis by a knob and to be periodically driven in rotation about the rotation axis by the main drive pin, during a drug dose setting. The driven wheel has a second rotation axis parallel or coaxial to said longitudinal axis and is configured to be periodically driven about the longitudinal axis by the drive wheel. The abutment element is configured to prevent the rotation of the drive wheel about the longitudinal axis when the knob has made a predetermined number of full and/or partial rotations about the longitudinal axis correlated to the predetermined drug volume.

13 Claims, 12 Drawing Sheets

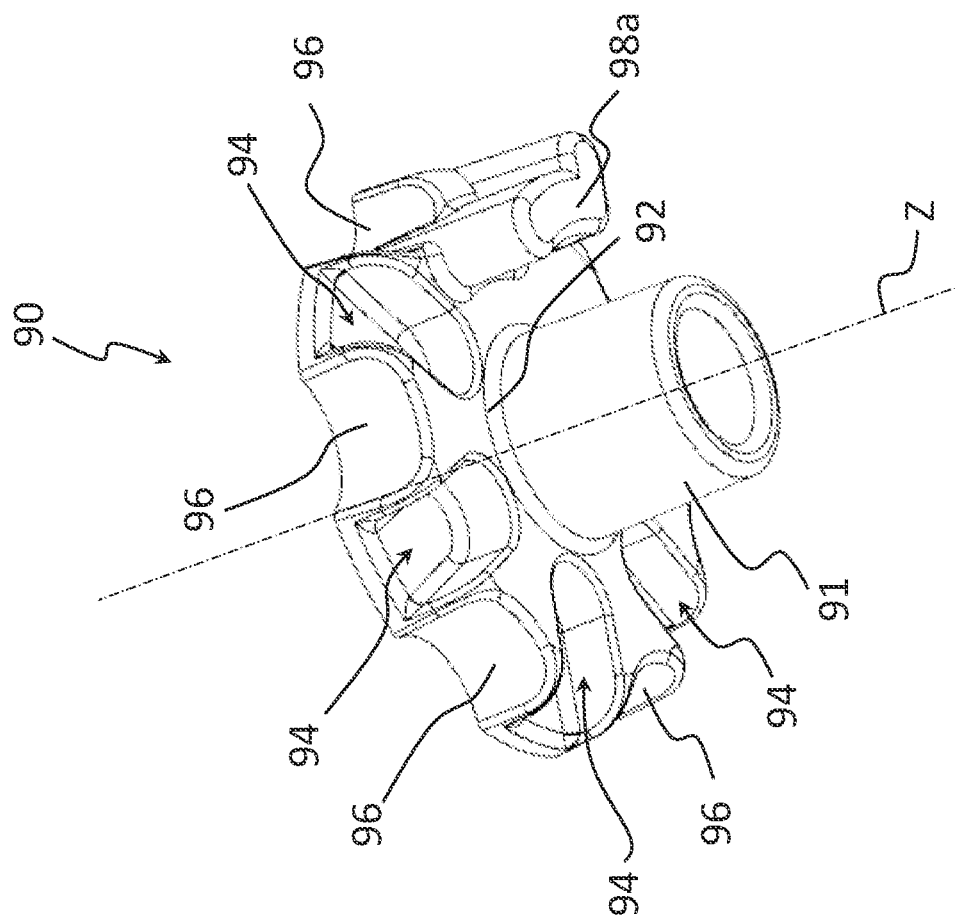
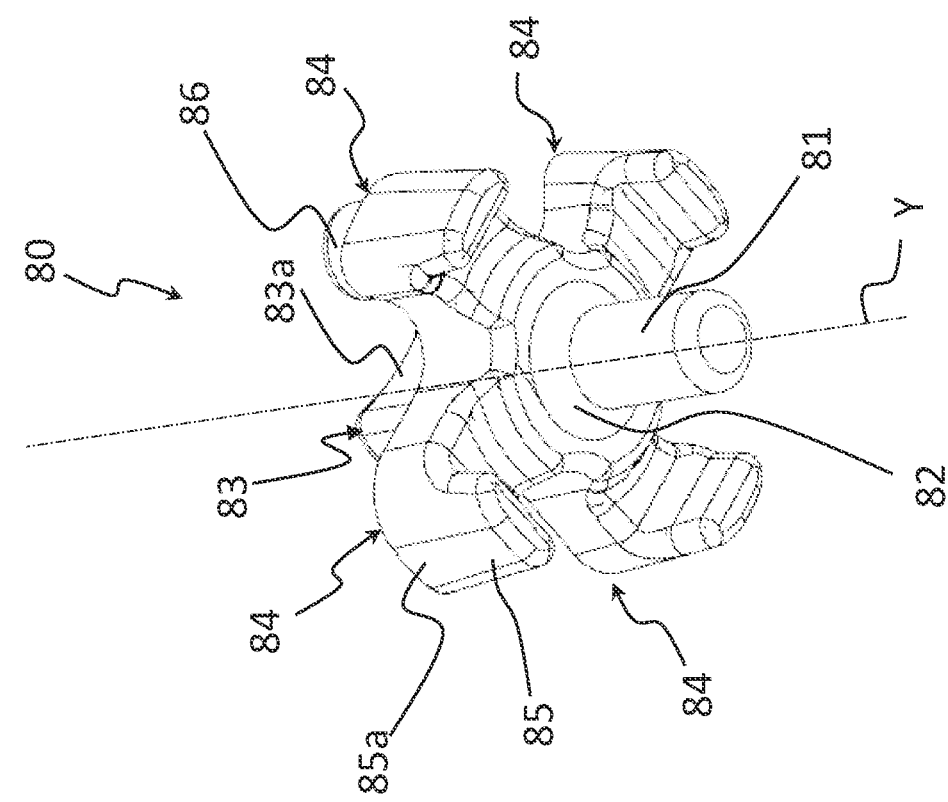

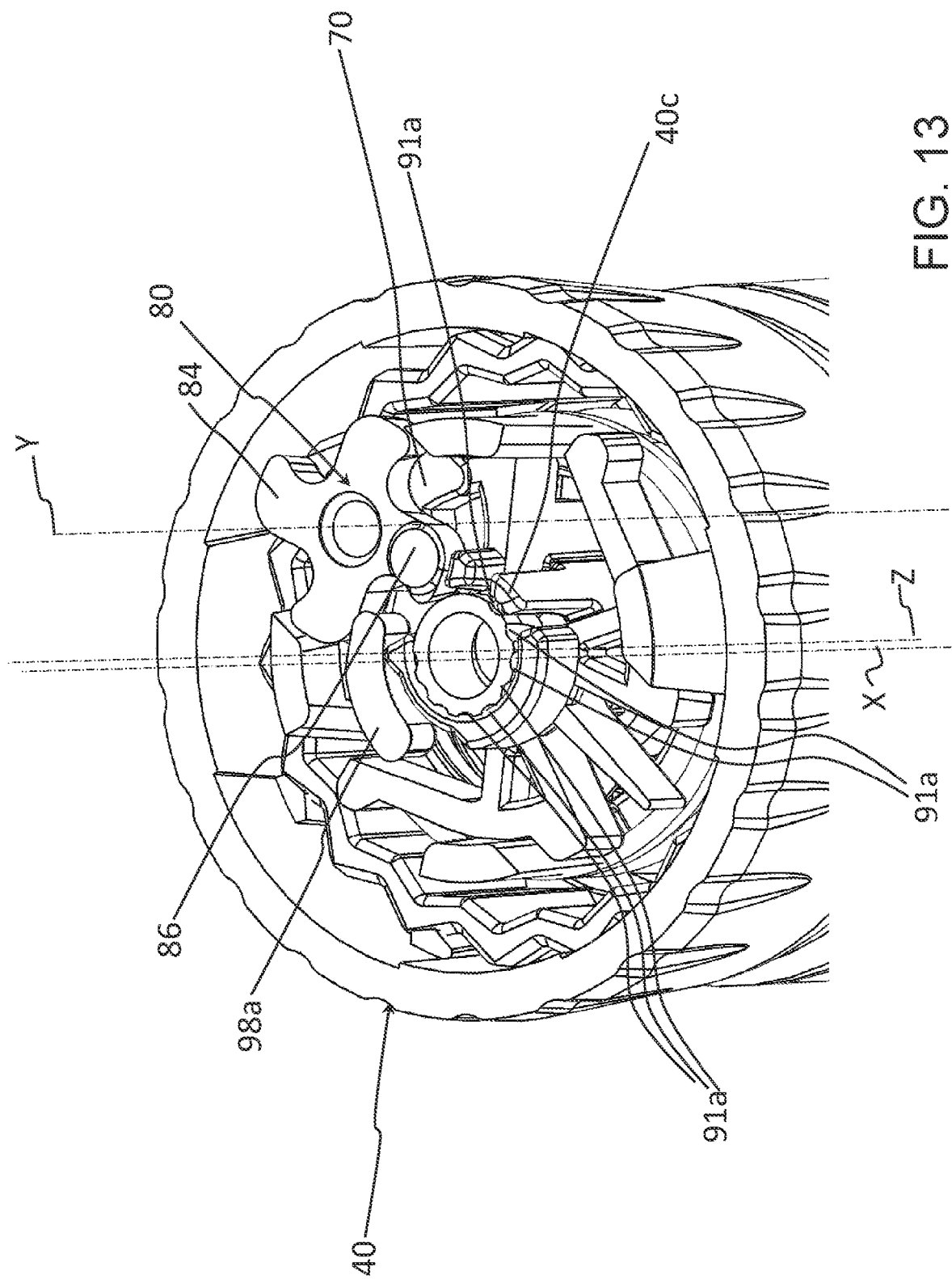

DRUG INJECTION DEVICE

CROSS REFERENCE

The present application claims priority to Italian Application No. 102021000032357 filed on Dec. 23, 2021, the entire disclosure of which is expressly incorporated by reference herein.

TECHNICAL FIELD

The present invention relates to a drug injection device, and, more particularly, to a drug injection device of the type allowing a user to set a desired dose of a predetermined drug volume contained in a drug container and to deliver the previously set desired dose to an injection site, the set and delivery operation being repeatable till the whole drug volume contained in the drug container is delivered. The drug container can be for example a cartridge housing or a syringe or any other element or device configured to contain the predetermined drug volume.

BACKGROUND

Examples of drug injection devices of the type discussed above are described in DE 202012001411U1 and U.S. Pat. No. 8,512,296B2. These devices are appreciated by the users as being compact and user-friendly.

U.S. Pat. No. 10,569,024B2 and US 2019/0366007A1 disclose drug injection devices which, in addition to comprising members configured to allow the user to set a desired dose before delivering such a dose, further comprise members configured to prevent the user to set a dose exceeding the dose volume remaining in the cartridge after having delivered one or more doses. In particular, in U.S. Pat. No. 10,569,024B2 such an exceeding dose is prevented to be set by an abutment between a stop member fixed to a piston rod and a stop member fixed to a nut member configured to move along the piston rod, whereas in US 2019/0366007A1 the abovementioned exceeding dose is prevented to be set by an abutment between a nut configured to move along a drive shaft and a worm gear fixed to an end of the drive shaft.

The Applicant has considered the benefit of preventing the user to be able to set a dose greater than the one currently available in the drug container.

Accordingly, the Applicant has thought to design a drug injection device wherein this benefit is achieved by a technical solution different from those of the prior art.

The Applicant has perceived that in most of the drug injection devices the users turn the knob to set a dose and then press the knob to deliver the dose. During any drug dose setting the knob moves along a first direction of the longitudinal axis while rotating about the longitudinal axis, whereas during any drug dose delivery the knob moves along a second direction opposite to the first direction without rotating about the longitudinal axis.

Hence, the Applicant has realized that depending on the size of the drug container (usually measured in terms of injection units) and on the size of the drug injection device (usually measured in terms of injection units as well), and in particular on the diameter of the knob, there is a known number of knob rotations about the longitudinal axis to reach the end of the drug container and deliver the whole drug volume originally provided in the drug container. Thus, preventing the knob from further rotating about the longitudinal axis after it has made the abovementioned known number of rotations actually prevents the user from setting a dose greater than the one currently available in the drug container.

SUMMARY

Accordingly, the Applicant has designed a last dose setting device associated with the knob and configured to lock the rotation of the knob when the abovementioned known number of knob rotations is reached.

Therefore, the present invention relates to a drug injection device that includes:
- a drug container extending along a longitudinal axis and configured to include a predetermined drug volume;
- a dose setting mechanism configured to set a drug dose to be delivered out of the drug container;
- a dose delivery mechanism configured to deliver the drug dose set by the dose setting mechanism;
- a knob configured to rotate about said longitudinal axis during a drug dose setting;
- a last dose setting device configured to prevent a user to set a drug dose greater than the drug volume remaining in the drug container after at least one previous drug dose delivery, wherein the last dose setting device comprises:
  - a main drive pin;
  - a drive wheel having a first rotation axis parallel to said longitudinal axis and configured to be driven in rotation about the longitudinal axis by the knob, and to be periodically driven in rotation about the first rotation axis by the main drive pin, during the drug dose setting;
  - a driven wheel having a second rotation axis parallel or coaxial to said longitudinal axis and configured to be periodically driven in rotation about the second rotation axis by the drive wheel;
  - an abutment element fixedly coupled to, or integrally formed with, the driven wheel and configured to prevent the rotation of the drive wheel about the longitudinal axis when the knob has made a predetermined number of full and/or partial rotations about the longitudinal axis correlated to the predetermined drug volume.

Throughout the present description and in the annexed claims, the term "axial" and the corresponding term "axially" are used to refer to a longitudinal direction of the injection device, which corresponds to the longitudinal direction of the drug container, whereas the term "radial" and the corresponding term "radially" are used to refer to any direction perpendicular to the abovementioned longitudinal direction. In particular, when referring to components which rotate about an axis, the terms "radial" and radially" are used to indicate any direction perpendicular to such an axis.

The term "distal" is used to indicate a position which is closer to the injection site (for example the skin of a patient) than to the hand of the user who handles the injection device during an injection operation, whereas the term "proximal" is used to indicate a position which is closer to the hand of the user who handles the injection device during the injection operation than to the injection site.

Consistently, a longitudinal direction oriented from the hand of the user who handles the injection device during the injection operation toward the injection site (for example the skin of a patient) is herein also referred to with the term "distal direction", whereas a longitudinal direction oriented from the injection site toward the hand of the user who handles the injection device during the injection operation is herein also referred to with the term "proximal direction".

The term "correlated" is used to indicate a mutual dependency relationship between two parameters, like for example a number of rotations and a volume. This means that the amount or size or extent of a first parameter is a function of (or depends on) the amount or size or extent of a second parameter and/or vice versa.

The last dose device provided in the drug injection device of the invention locks the knob rotation when desired, that is when the knob has made the predetermined number of rotations about the longitudinal axis, by locking the rotation of the drive wheel about its rotation axis. The lock of the drive wheel rotation occurs when the drive wheel engages the main drive pin and the abutment element prevents the drive wheel to be driven in rotation about its rotation axis by the main drive pin. It is possible to correlate the rotational movement of the abutment element with respect to the drive wheel with the rotational movement of the drive wheel with respect to the main drive pin, and thus with the rotational movement of knob, in order to lock the rotation of the drive wheel about its rotation axis, and thus the rotation of the knob about the longitudinal axis, when desired, that is when the knob has made a predetermined number of rotations about the longitudinal axis.

Preferred features of the drug injection device of the invention are disclosed below, each of these features being provided individually or in combination with the other preferred features.

Preferably, the injection device is of the pen-type, so as to allow an easy portability, handling, storing and operation of the injection device by the user.

The injection device can be of the re-usable or disposable type, whereas the disposable use is the most preferred one.

Preferably, the knob is configured to move along a first direction of said longitudinal axis while rotating about said longitudinal axis during the drug dose setting and to move along a second direction opposite to said first direction without rotating about said longitudinal axis during a drug dose delivery.

In some preferred embodiments, the main drive pin is stationary.

In other preferred embodiments, the main drive pin is configured to move along said first direction without rotating about said longitudinal axis during the drug dose setting and to move along said second direction without rotating about said longitudinal axis during the drug dose delivery.

In some preferred embodiments, when the knob has made said predetermined number of full and/or partial rotations about the longitudinal axis, said drive wheel abuts against said main drive pin and said abutment element.

In other preferred embodiments, the last dose setting device further includes a stop member configured to abut against said abutment element and to prevent the rotation of the driven wheel about the second rotation axis when the knob has made said predetermined number of full and/or partial rotations about the longitudinal axis and said drive wheel abuts against said main drive pin.

In anyone of the abovementioned preferred embodiments, preferably, before setting a first drug dose the main drive pin, the drive wheel and the driven wheel are arranged with respect to each other so that when the knob has made the predetermined number of full and/or partial rotations about the longitudinal axis the predetermined drug volume is delivered. Therefore, the initial reciprocal arrangement of the main drive pin, the drive wheel and the driven wheel depends on the predetermined number of full and/or partial knob rotations to be made, which depends in turn on the predetermined drug volume contained in the drug container.

Preferably, the knob comprises a hollow body.

Preferably, said drive wheel, said driven wheel and said main drive pin are housed in said hollow body. In this way, the injection device of the invention has a compact longitudinal extension.

Preferably, said main drive pin drives in rotation the drive wheel about the first rotation axis by a predetermined first angle every full rotation of the knob about the longitudinal axis. The predetermined first angle is preferably a submultiple of 360°, so that the drive wheel makes a full rotation about the first rotation axis after a predetermined number of full rotations of the knob about the longitudinal axis.

Preferably, the drive wheel drives in rotation the driven wheel about the second rotation axis by a predetermined second angle every full rotation of the drive wheel about the first rotation axis.

Preferably, said drive wheel comprises a first central body and a predetermined number of arms extending substantially radially from the first central body. The drive wheel is driven in rotation by the predetermined first angle when each arm abuts against the main drive pin. Each time an arm abuts against the main drive pin the drive wheel rotates with respect to the knob.

Preferably, said arms are equally spaced from each other.

Preferably, at least one of the arms has an auxiliary drive pin extending substantially parallel to said longitudinal axis and configured to periodically engage with said driven wheel during rotation of the drive wheel about the first rotation axis. The driven wheel is driven in rotation by the predetermined second angle when the auxiliary drive pin engages with said driven wheel and the abutment element has not yet engaged the drive wheel.

Preferably, said arms are equally spaced apart from each other about the first rotation axis. In this way, each time the drive wheel engages with the main drive pin the drive wheel rotates by the same predetermined first angle. For example, if the arms are four, each time the drive wheel engages with the main drive pin the drive wheel rotates by 90°.

Preferably, said driven wheel comprises a second central body and a predetermined number of slots extending substantially radially from the second central body and configured to receive said auxiliary drive pin during rotation of the drive wheel about the first rotation axis. The radial extension of each slot is correlated with the predetermined second angle.

Preferably, at least some of said slots are equally spaced apart from each other about the second rotation axis. In this way, each time the arm with the auxiliary drive pin of the drive wheel engages with the driven wheel it is housed in a respective slot.

Preferably, the last dose setting device comprises first members configured to prevent the rotation of the drive wheel about the first rotation axis when the drive wheel rotates about the longitudinal axis and does not engage with the main drive pin.

Preferably, the last dose setting device comprises second members configured to prevent the rotation of the driven wheel about the second rotation axis when the driven wheel rotates about the longitudinal axis and does not engage with the auxiliary drive pin.

The provision of the abovementioned first and second members allows to avoid undesired rotations of the drive wheel and driven wheel, respectively, about their rotation axis during rotation of the drive wheel and driven wheel about the longitudinal axis. Indeed, in order to have an efficient operation of the last dose setting device, it is desired that the drive wheel rotates about its rotation axis only when the drive wheel engages the main drive pin and the driven wheel rotates about its rotation axis only when the driven wheel is engaged by the drive wheel.

In some preferred embodiments, the first members comprise a circumferential rail configured to engage with the arms of said drive wheel during rotation of the drive wheel about the longitudinal axis. Such a circumferential rail guides the rotation of the drive wheel about the longitudinal axis and prevents rotation of the drive wheel about its rotation axis when the drive wheel does not engage with the main drive pin. Every full rotation of the drive wheel about the longitudinal axis the circumferential rail engages with one of the arms, and in particular with the arm which precedes the arm which engages with the main drive pin.

Preferably, the circumferential rail is interrupted at the main drive pin to allow the rotation of said drive wheel about its rotation axis. This rotation allows the circumferential rail to engage with another arm.

In different preferred embodiments, the first members comprise a predetermined number of plane faces provided on a rotation pin of the drive wheel and an insert which moves integrally with the knob.

Preferably, the number of the plane faces provided on the rotation pin of the drive wheel is correlated to the number of arms of the drive wheel, more preferably it is equal to the number of arms of the drive wheel.

Preferably, the position of the plane faces provided on the rotation pin of the drive wheel about the rotation axis Y is correlated to said predetermined first angle, more preferably the abovementioned plane faces are spaced apart from each other by an angle equal to the predetermined first angle.

The coupling between each plane face of the rotation pin of the drive wheel and the insert resists to relative rotation of the rotation pin of the drive wheel with respect to the insert when the drive wheel does not engage with the main drive pin. When the drive wheel is driven in rotation about its rotation axis by the engagement of one of its arms with the main drive pin, the plane face of the rotation pin of the drive wheel is decoupled from the insert and a rotation of the rotation pin with respect to the insert occurs. After such a relative rotation a new configuration is reached wherein another plane face of the rotation pin of the drive wheel is coupled with the insert, thus again preventing rotation of the drive wheel about its rotations axis until another arm engages with the main drive pin.

In some preferred embodiments, the second members comprise a D-shaped protrusion extended from the drive wheel substantially parallel to said longitudinal axis on the same side of the auxiliary drive pin and having a straight side of the "D" facing towards the auxiliary drive pin.

Preferably, said driven wheel comprises a plurality of recesses configured to house the D-shaped protrusion when the auxiliary drive pin does not engage said slots.

In this way, the D-shaped protrusion engages the recesses of the driven wheel during the rotation of the drive wheel about the longitudinal axis also when the auxiliary drive pin does not engage said slots. When the auxiliary drive pin engages said slots a relative rotation of the driven wheel with respect to the drive wheel is performed. When the auxiliary drive pin does not engage said slots a relative rotation of the driven wheel with respect to the drive wheel is prevented by the coupling between the D-shaped protrusion and the recesses of the driven wheel.

In different preferred embodiments, the second members comprise a plurality of notches formed on an outer surface of a rotation pin of the driven wheel and a ratchet pin which rotates integrally with the knob.

During rotation of the knob about the longitudinal axis, the coupling between ratchet pin and notch causes the driven wheel to be driven in rotation about the longitudinal axis and to prevent rotation of the driven wheel with respect to its rotation axis. Each time the auxiliary drive pin of the drive wheel engages a slot in the driven wheel, the ratchet pin is forced out of the notch and the driven wheel rotates about its rotation axis. After such a relative rotation a new configuration is reached wherein the ratchet pin engages with another notch, thus preventing the rotation of the driven wheel about its rotation axis until the auxiliary drive pin engages with another slot.

In a first preferred embodiment of the invention, said main drive pin is provided on a sleeve configured to slide along said longitudinal axis integral with the knob.

In a second preferred embodiment of the invention, said main drive pin is provided on a ring element fixedly coupled to said sleeve.

In other preferred embodiments of the invention, the main drive pin does not slide along said longitudinal axis.

Preferably, the knob is closed on the opposite side with respect to drug container by a removable cover plate. The cover plate can be removed to provide the initial arrangement of the main drive pin, the drive wheel and the driven wheel, before setting a first drug dose.

BRIEF DESCRIPTION OF THE DRAWINGS

Further features and advantages of the present invention will become clearer from the following detailed description of preferred embodiments thereof, made with reference to the attached drawings and given for indicating and not limiting purposes. In such drawings:

FIGS. 6-8 are perspective view of three components of the last dose setting device shown in FIGS. 4 and 5;

FIG. 13 is a schematic perspective view of a proximal part of the injection device of FIG. 3, showing a transversal section of a fourth embodiment of a last dose setting device in a first configuration thereof.

DETAILED DESCRIPTION

Figure 1:
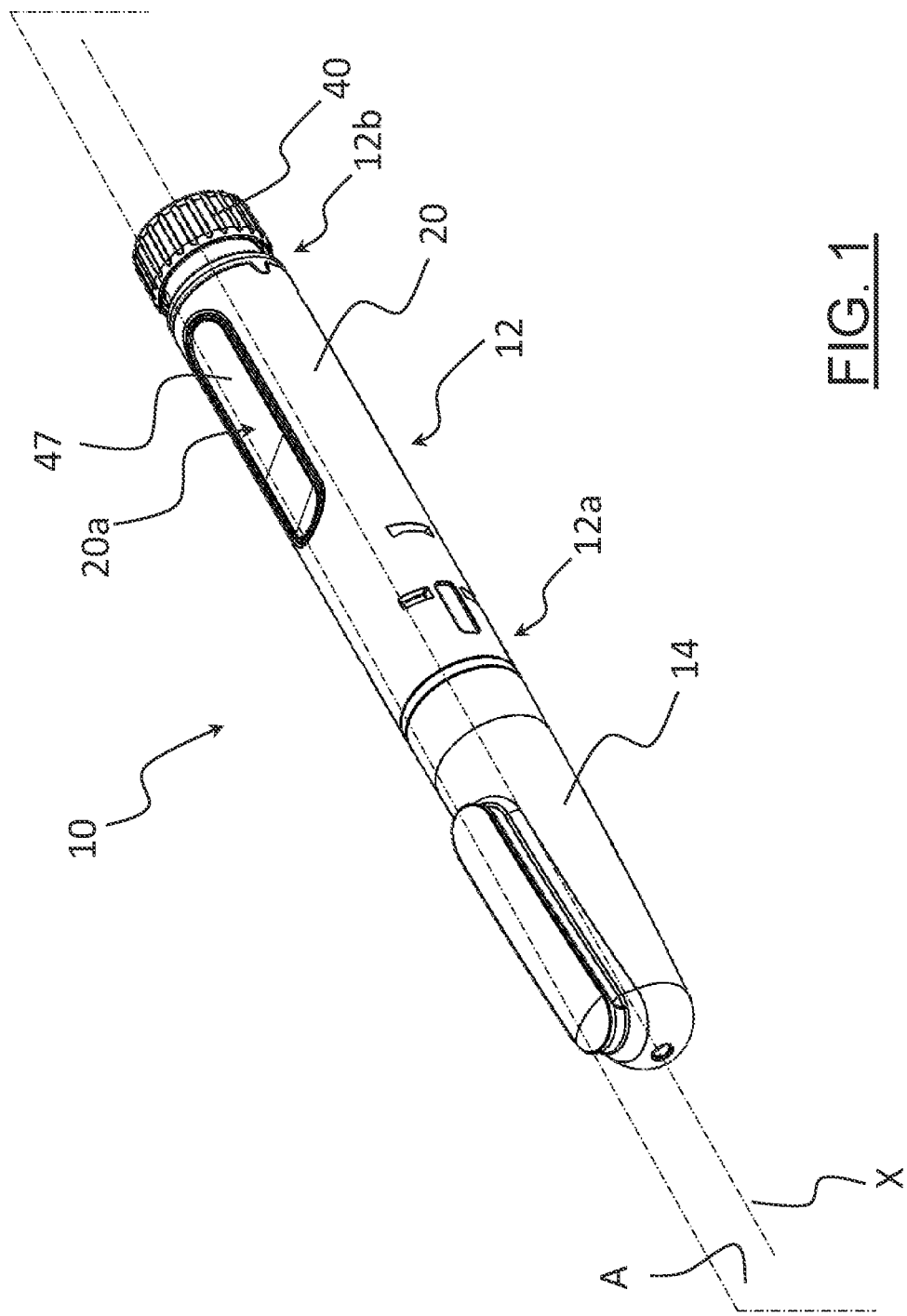
FIG. 1 is a schematic perspective view of an embodiment of a drug injection device according to the present invention.

An embodiment of a drug injection device 10 according to the present invention is shown in FIG. 1.

The injection device 10 is of the pen-type and extends along a central longitudinal axis X.

The injection device 10 includes a main body 12 and a cap case 14 removably associated with the main body 12 at a first free end 12a of the main body 12.

Both the main body 12 and the cap case 14 when the latter is coupled to the main body 12, extend coaxially to the longitudinal axis X.

Figure 2:
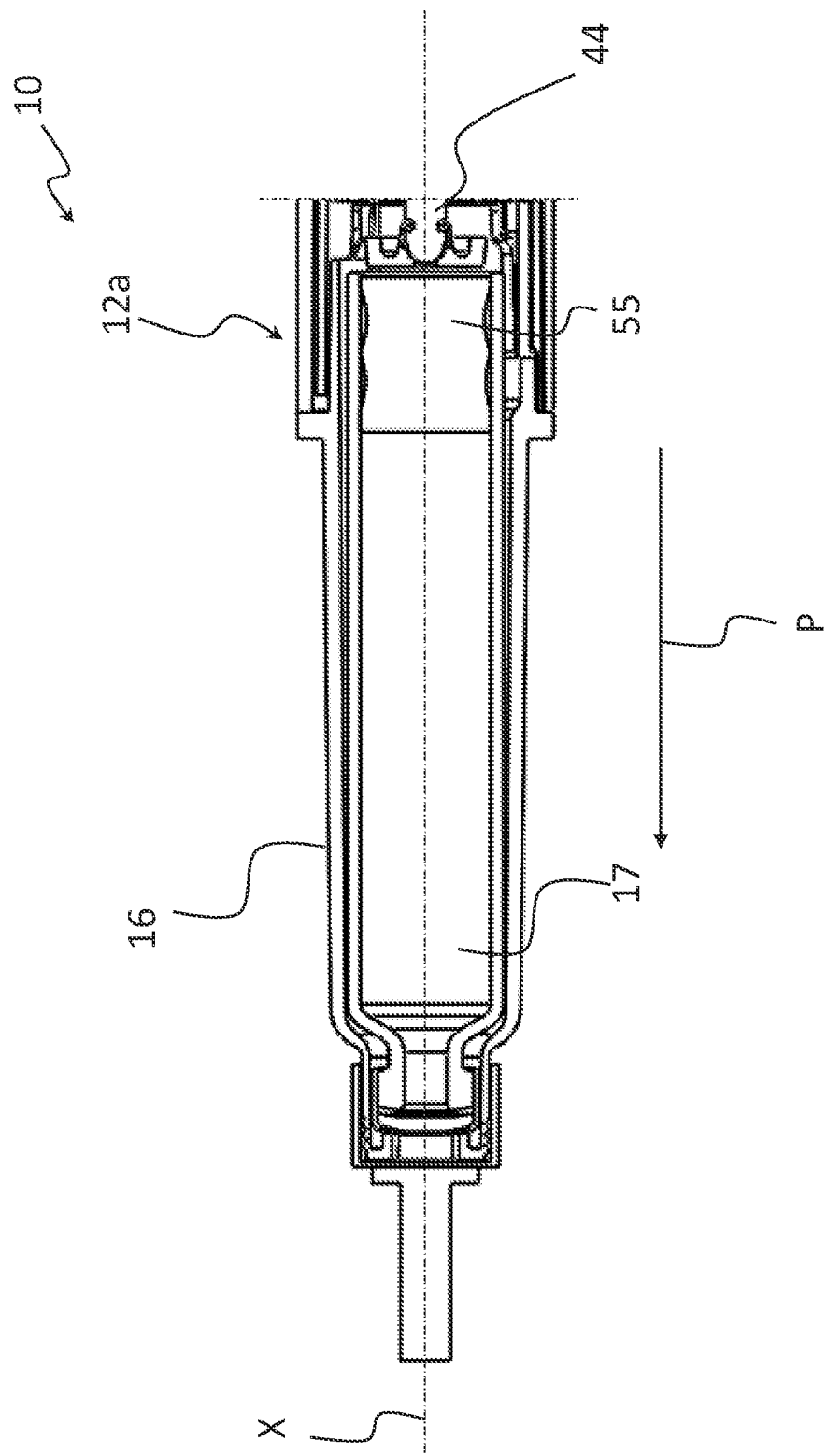
FIG. 2 is a schematic sectional view of a distal part of the injection device of FIG. 1 taken at the sectional plane labelled with A in FIG. 1.

As shown in FIG. 2, a drug container 16 extending coaxially with the longitudinal axis X is removably coupled to the main body 12 at the first free end 12a so as to be housed within the cap case 14 when the latter is coupled to the main body 12. The drug container 16 is configured to include a predetermined drug volume to be delivered.

In the embodiment of FIG. 2, the drug container 16 is a cartridge housing which houses a cartridge 17 including the predetermined drug volume. In embodiments not shown, the drug container 16 can be a syringe.

As shown in FIG. 1, the main body 12 comprises an outer case 20, which preferably is substantially cylindrically-shaped.

A dose setting mechanism 30 and a dose delivery mechanism 35 are provided within the outer case 20. The dose setting mechanism 30 is configured to allow a user to set a drug dose to be delivered out of the cartridge 17, whereas the dose delivery mechanism 35 is configured to allow the user to deliver the drug dose set by the dose setting mechanism 30.

As many different kinds of dose setting mechanism 30 and dose delivery mechanism 35 can be foreseen in the injection device 10 of the invention, they are not described in detail herein. For example, the dose setting mechanism 30 and dose delivery mechanism 35 can be of the same type as described in DE 202012001411U1 and U.S. Pat. No. 8,512, 296B2. In this specific case and as it will be clearer from the description below, the dose setting mechanism 30 of the injection device 10 differs from the one of the devices of these two prior art documents in that it further includes a last dose setting device 60, shown in FIGS. 4 and 5 and described in more details below with reference to FIGS. 4-8.

The dose setting mechanism 30 and the dose delivery mechanism 35 share a knob 40 provided at a second free end 12b of the main body 12 opposite the first free end 12a thereof and a dose setting service element arranged within the outer case 20 coaxially to the longitudinal axis X and having a free end operatively connected to the knob 40.

Figure 3:
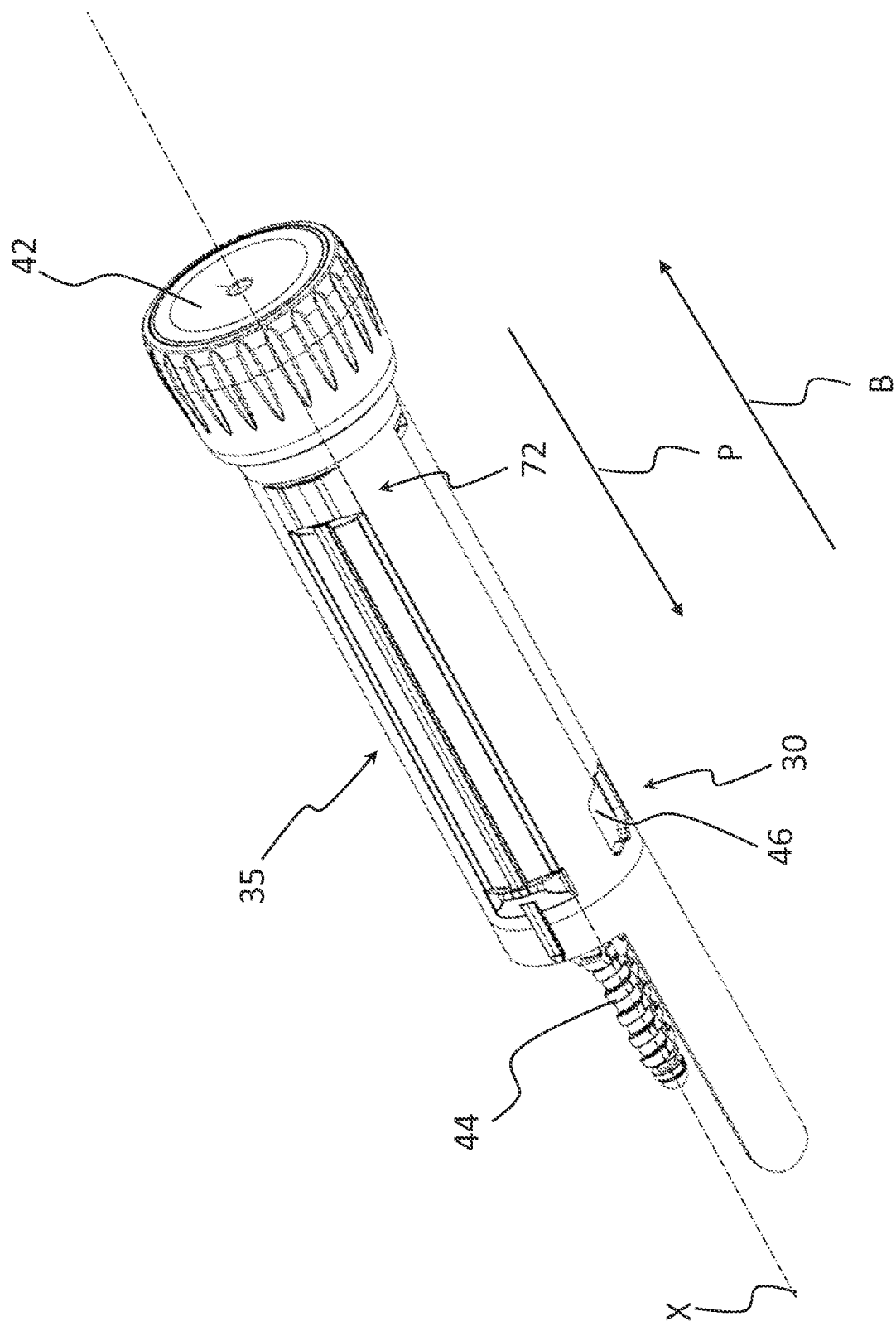
FIG. 3 is a schematic perspective view of some components provided in a proximal part of the injection device of FIG. 1.

In the embodiment herein shown (FIGS. 2 and 3), the abovementioned dose setting service element is a piston rod 44 extending coaxially to the longitudinal axis X.

The knob 40 is configured to be driven by the user in rotation clockwise and counter-clockwise about the longitudinal axis X during a drug dose setting and to be pushed by the user along a longitudinal (or distal) direction P parallel to the longitudinal axis X during a drug dose delivery.

Figure 4:
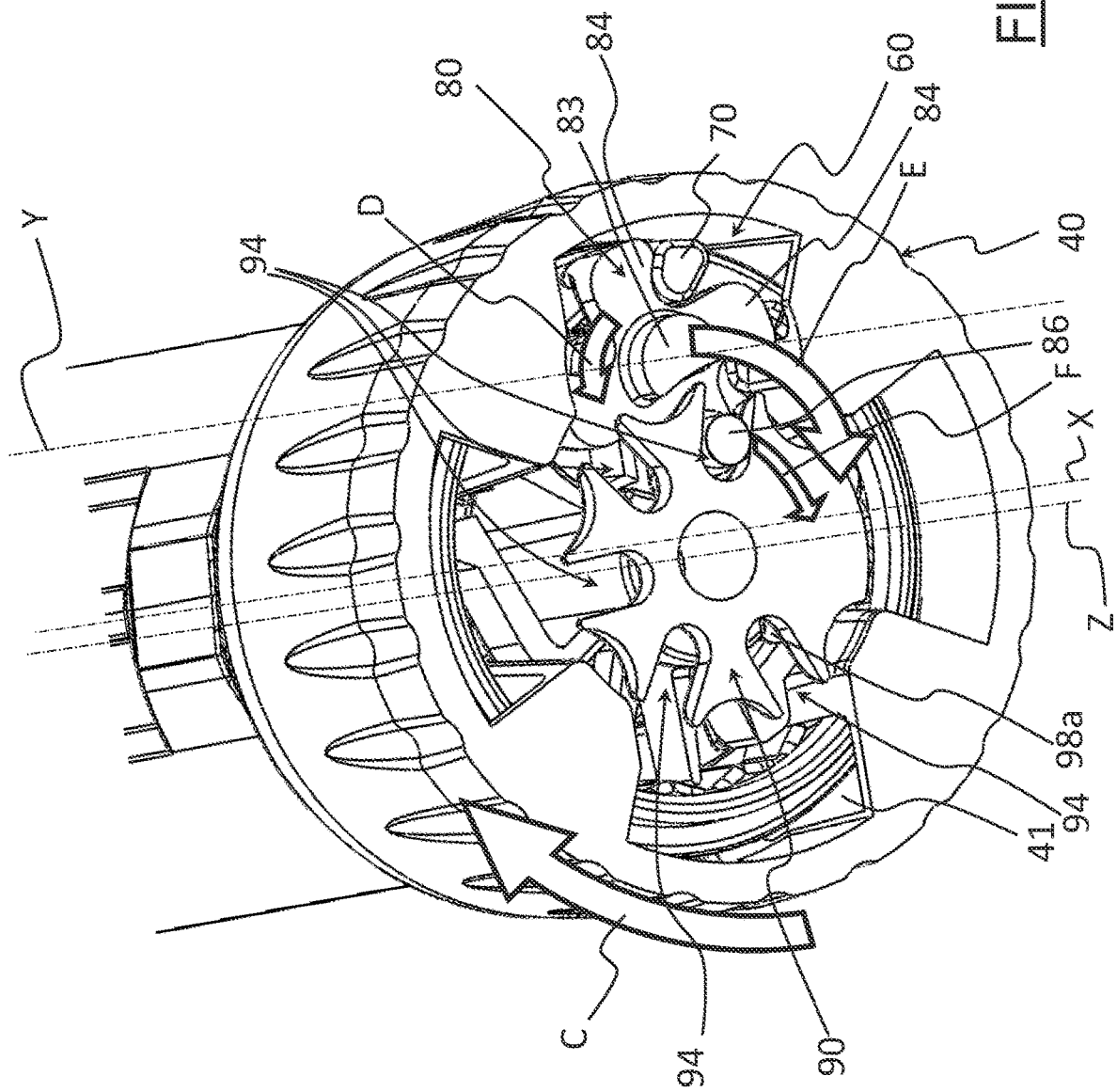
FIG. 4 is a schematic perspective view of a proximal part of the injection device of FIG. 3, showing a first transversal section of a first embodiment of a last dose setting device in a first configuration thereof.

The rotation is herein intended as clockwise or counter-clockwise when looking a right side view of the injection device 10 when the latter is positioned as shown in FIG. 1, that is when looking at the knob 40 from a side opposite to the side where the cartridge 17 is provided. The clockwise direction of rotation of the knob 40 is indicated in FIG. 4 by the arrow C.

During the drug dose setting, the knob 40 moves along a direction B opposite to the direction P while rotating about the longitudinal axis X.

During a drug dose delivery, the knob 40 moves along the direction P without rotating about the longitudinal axis X.

A clutch device is provided within the outer case 20 to switch the injection device 10 between a dose setting configuration wherein the clutch device is operatively connected to the knob 40 and operatively connects the knob 40 to the dose setting mechanism 30, and a dose delivery configuration wherein the clutch device is operatively disconnected from the knob 40 and the latter is operatively connected to the dose delivery mechanism 35.

The piston rod 44 is configured to move along said longitudinal direction toward the drug container 16 (thus along the distal direction P) during the drug dose delivery.

In the dose setting configuration, the piston rod 44 rotates about the longitudinal axis X and moves along the longitudinal direction B, whereas in the dose delivery configuration the piston rod 44 moves along the longitudinal direction P and is prevented to rotate about the longitudinal axis X.

The piston rod 44 is coupled to a dose setting sleeve 46 (FIG. 3) which rotates about the longitudinal axis X both in the dose setting configuration and in the dose delivery configuration. In the dose setting configuration, the rotation of the dose setting sleeve 46 and of the piston rod 44 is driven by the clutch device which in turn is driven by the rotation of the knob 40 about the longitudinal axis X, whereas in the dose delivery configuration the rotation of the dose setting sleeve 46 is caused by an axial thrust exerted by the user on the knob 40 along the longitudinal direction P.

The dose setting sleeve 46 comprises an outer surface 47 (FIG. 1) having a plurality of numbers (or generally indicia, not shown), each number being correlated to a respective dose of all the settable doses.

The dose setting sleeve 46 is housed within a sleeve 72 which slides along the longitudinal axis X integral with the knob 40.

As shown in FIG. 1, a display window 20a is formed in the outer case 20.

The user rotates the knob 40 clockwise or counter-clockwise till the number correlated to the desired dose to be set and delivered is displayed through at the display window 20a, thus providing the user with a visual indication about the dose actually set. Rotation in both directions during the dose setting operation allows the user to set the desired dose in case he/she initially sets a dose greater or lower than the desired dose.

Once the desired dose has been set, the user pushes the knob 40 along the longitudinal direction P to deliver such a dose. The axial movement of the knob 40 causes the clutch device to switch the injection device 10 from the dose setting configuration to the dose delivery configuration. In the latter configuration the knob 40 is prevented to rotate.

A stopper 55 (FIG. 2) is coupled to the free end of the piston rod 44 opposite to the knob 40. The stopper 55 is initially inserted within the cartridge 17, provided within the drug container 16, at a free end of the cartridge 17 located at the free end 12a of the main body 12. Due to the axial movement of the piston rod 44 caused by the axial movement of the knob 40 during the dose delivery operation, the stopper 55 axially moves within the cartridge 17 along the longitudinal direction P toward the opposite free end of the cartridge 17 thus forcing the desired dose to exit from the cartridge 17 at the opposite free end thereof.

The knob 40 comprises a hollow body 41 which is closed on the opposite side with respect to the drug container 16 by a removable cover plate 42.

Figure 5:
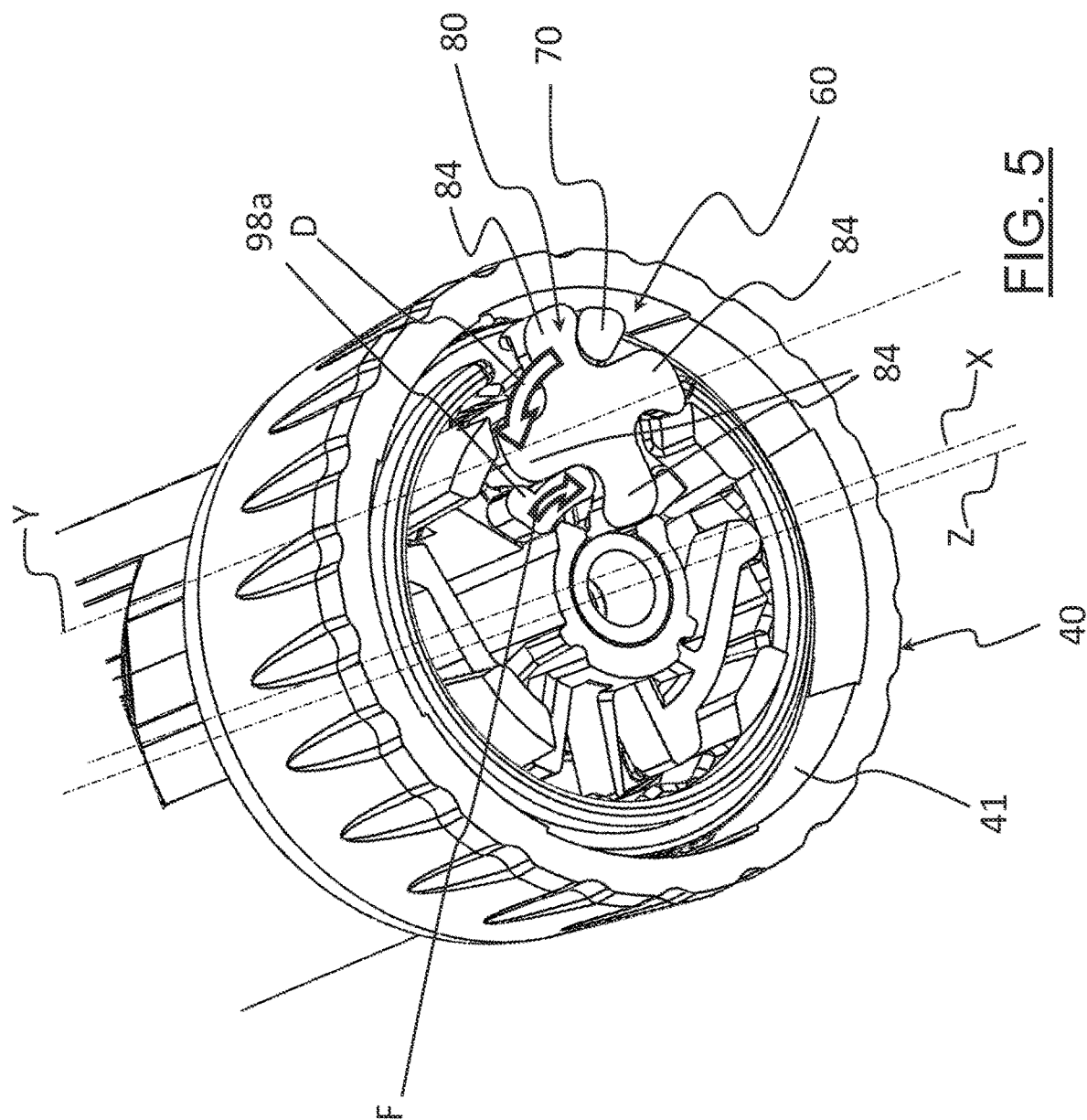
FIG. 5 is a schematic perspective view of the proximal part of FIG. 4, showing a second transversal section of the last dose setting device of FIG. 4 in a final configuration thereof, the second transversal section being less proximal than the first transversal section.
Figure 8:
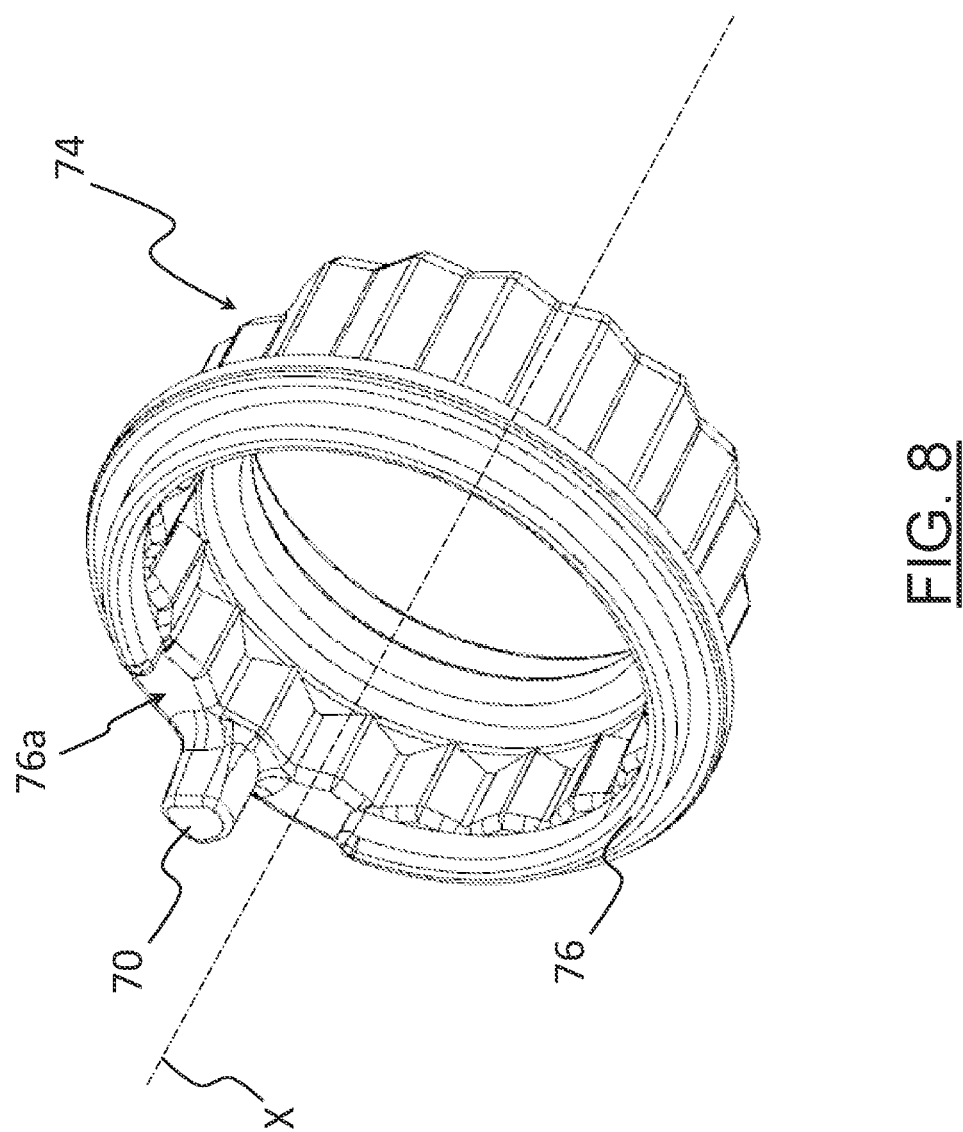

As shown in FIGS. 4 and 5, a last dose setting device 60 is arranged within the hollow body 41 of the knob 40 in order to prevent the user to set a dose greater than the one remaining in the cartridge 17 after the previous dose delivery/ies.

The last dose setting device 60 comprises, inter alia, a main drive pin 70, a drive wheel 80 and a driven wheel 90, which are all housed inside the hollow body 41.

An abutment element 98a is integrally formed with the driven wheel 90 (FIG. 7).

The main drive pin 70 extends along a direction parallel to the longitudinal axis X.

In the embodiment herein shown (FIG. 8), the main drive pin 70 is fixedly provided on a ring element 74 fixedly coupled to the sleeve 72. In a different embodiment not shown, the main drive pin 70 is fixedly provided directly on the sleeve 72.

The ring element 74 comprises, on a proximal side thereof, a circumferential rail 76 with an interruption 76a at the main drive pin 70.

The main drive pin 70 moves along the direction B without rotating about the longitudinal axis X during the drug dose setting and moves along the direction P without rotating about the longitudinal axis X during the drug dose delivery.

As shown in FIG. 6, the drive wheel 80 comprises a rotation pin 81 having a rotation axis Y parallel to the longitudinal axis X. The rotation pin 81 extends on a distal side of the drive wheel 80. The rotation pin 81 is connected to the knob 40 so that, during the drug dose setting, the drive wheel 80 is driven in rotation about the longitudinal axis X by the knob 40.

The drive wheel 80 further comprises a central body 82 and four arms 84 extending substantially radially from the central body 82. The arms 84 are equally spaced apart from each other about the rotation axis Y by an angle of 90°.

During the drug dose setting, the drive wheel 80 rotates with the knob 40 about the longitudinal axis X. Each time an arm 84 engages the main drive pin 70 the latter drives in rotation the drive wheel 80 about the rotation axis Y, so that a relative rotation of the drive wheel 80 with respect to the knob 40 is performed.

In particular, the main drive pin 70 drives in rotation the drive wheel 80 by a first angle of 90° every full rotation of the knob 40 about the longitudinal axis X. Therefore, every four full rotation of the knob 40 about the longitudinal axis X, the drive wheel 80 is driven in rotation about the rotation axis Y by 360°.

One of the arms 84 has an auxiliary drive pin 86 extending substantially parallel to the longitudinal axis X. The auxiliary drive pin 86 extends on a proximal side of the drive wheel 80.

The drive wheel 80 further comprises a D-shaped protrusion 83 extended substantially parallel to the longitudinal axis X on the proximal side of the drive wheel 80, i.e., on the same side of the auxiliary drive pin 86. A straight side 83a of the "D" of the D-shaped protrusion 83 faces towards the auxiliary drive pin 86.

Each arm 84 has an engagement protrusion 85 extended substantially parallel to the longitudinal axis X on the distal side of the drive wheel 80 and configured to engage with the circumferential rail 76 of the ring element 74 during rotation of the drive wheel 80 about the longitudinal axis X. Each engagement protrusion 85 extends at the free end portion 85a of the respective arm 84. Every full rotation of the drive wheel 80 about the longitudinal axis X one of the arms 84 engages with the circumferential rail 76. Every 90° rotation of the drive wheel 80 about the rotation axis Y a different arm 84 engages with the circumferential rail 76.

The circumferential rail 76 prevents rotation of the drive wheel 80 about its rotation axis Y during rotation of the drive wheel 80 about the longitudinal axis X when the main drive pin 70 does not engage with any of the arms 84. The interruption 76a of the circumferential rail 76 allows the rotation of the drive wheel 80 about the rotation axis Y when an arm 84 of the drive wheel 80 engages the main drive pin 70.

As shown in FIG. 7, the driven wheel 90 comprises a rotation pin 91 which has a rotation axis Z parallel to the longitudinal axis X.

In an embodiment not shown, the rotation pin 91 is coaxial to the longitudinal axis X.

The rotation pin 91 extends on a distal side of the driven wheel 90.

The driven wheel 90 further comprises a central body 92 and a plurality of slots 94 extending substantially radially from the central body 92. In the embodiment herein shown (FIGS. 4 and 7), the slots 94 are five and are spaced apart from each other about the rotation axis Z.

The slots 94 are closed on a proximal side of the driven wheel 90 and open on a distal side of the driven wheel 90.

The slots 94 receive the auxiliary drive pin 86 during rotation of the drive wheel 80 about the rotation axis Y. Each time during the drug dose setting, and in particular during rotation of the drive wheel 80 about the rotation axis Y, the auxiliary drive pin 86 engages a slot 94, the drive wheel 80 drives the driven wheel 90 in rotation about the rotation axis Z.

As shown in FIG. 7, the driven wheel 90 further comprises a plurality of recesses 96, each one provided between two adjacent slots 94.

The recesses 96 extends substantially parallel to the rotation axis Z and are C-shaped when seen in a cross section (FIG. 4).

Each recess 96 houses the D-shaped protrusion 83 during rotation of the drive wheel 80 about the longitudinal axis X and prevents rotation of the driven wheel 90 about its rotation axis Z when the auxiliary drive pin 86 does not engage the slots 94.

When the auxiliary drive pin 86 engages the slots 94 a relative rotation of the driven wheel 90 with respect to the drive wheel 80 is performed. In particular, every full rotation of the drive wheel 80 about the rotation axis Y, the auxiliary drive pin 86 of the drive wheel 80 drives in rotation the driven wheel 90 about the rotation axis Z by a predetermined angle which depends on the radial extension of the slots 94.

FIG. 4 shows a configuration of the last dose setting device 60 which occurs during the drug dose setting.

In such a configuration a first arm 84 of the drive wheel 80 abuts against the main drive pin 70 and the auxiliary drive pin 86 is housed within a first slot 94, so that a rotation about the longitudinal axis X in the clockwise direction of the knob 40 (arrow C) causes the drive wheel 80, which in turn rotates about the longitudinal axis X with the knob 40 (arrow E), to be driven in rotation by the main drive pin 70 in the counter-clockwise direction about the rotation axis Y (arrow D) by 90°. The rotation about the rotation axis Y of the drive wheel 80 causes the rotation about the rotation axis Y of the auxiliary drive pin 86, which drives in rotation the driven wheel 90 in the clockwise direction (arrow F) about the rotation axis Z, so that a relative rotation of the driven wheel 90 with respect to the drive wheel 80 is performed. Such a relative rotation causes the exit of the auxiliary drive pin 86 from the first slot 94.

Starting from the configuration of FIG. 4, after four full rotations of the knob 40, the auxiliary drive pin 86 engages the second slot 94, i.e., the slot 94 adjacent to the first slot 94 in the counter-clockwise direction about the rotation axis Z.

In the same manner, after other four full rotations of the knob 40, the auxiliary drive pin 86 engages the third slot 94, after other four full rotations of the knob 40 the auxiliary drive pin 86 engages the fourth slot 94 and after other four full rotations of the knob 40 the auxiliary drive pin 86 engages the fifth slot 94.

FIG. 5 shows a configuration of the last dose setting device 60 wherein the auxiliary drive pin 86 of the drive wheel 80 engages the fifth slot 94 and one of the arms 84 abuts against the abutment element 98a.

The abutment element 98a reaches the position of FIG. 5 when the knob 94 has made a predetermined number of full and/or partial rotations about the longitudinal axis X correlated to the predetermined drug volume to be dispensed. In the configuration of FIG. 5 any further rotation of the drive wheel 80 about the longitudinal axis X is prevented.

Indeed, FIG. 5 shows that the arm 84 of the drive wheel 80 is abutting against the main drive pin 70, so that the drive wheel 80 tends to be driven in rotation by the main drive pin 70 in the counter-clockwise direction about the rotation axis Y according to arrow D. Accordingly, the auxiliary drive pin 86 tends to drive in rotation the driven wheel 90 in the clockwise direction about the rotation axis Z according to arrow F. However, the driven wheel 90 cannot perform such a rotation because of the abutment between one of the arms 84 of the drive wheel 80 and the abutment element 98a.

Before the first drug dose setting, a specific angular position of the drive wheel 80 with respect to the main drive pin 70 and of the driven wheel 90 with respect to the drive wheel 80 is selected in order to reach the final configuration of FIG. 5 after a predetermined number of full and/or partial rotations of the knob 40 about the longitudinal axis X, this number depending on the predetermined drug volume contained in the cartridge 17.

Should the user try to set a dose greater than the one currently and actually available in the cartridge 17, the abutment element 98a prevents further relative rotation between the drive wheel 80 and the driven wheel 90, thus preventing the user to set such a dose.

While in the embodiments described above the main drive pin 70 moves along the direction B during the drug dose setting and along the direction P during the drug dose delivery, other embodiments are provided in which the main drive pin 70 does not move along the directions B and P.

Analogously, while in the embodiments described above the knob 40 moves along the direction B during the drug dose setting and along the direction P during the drug dose delivery, the movements of the knob 40 along the directions B and P is not essential for the operation of the last dose setting device 60.

Figure 9:
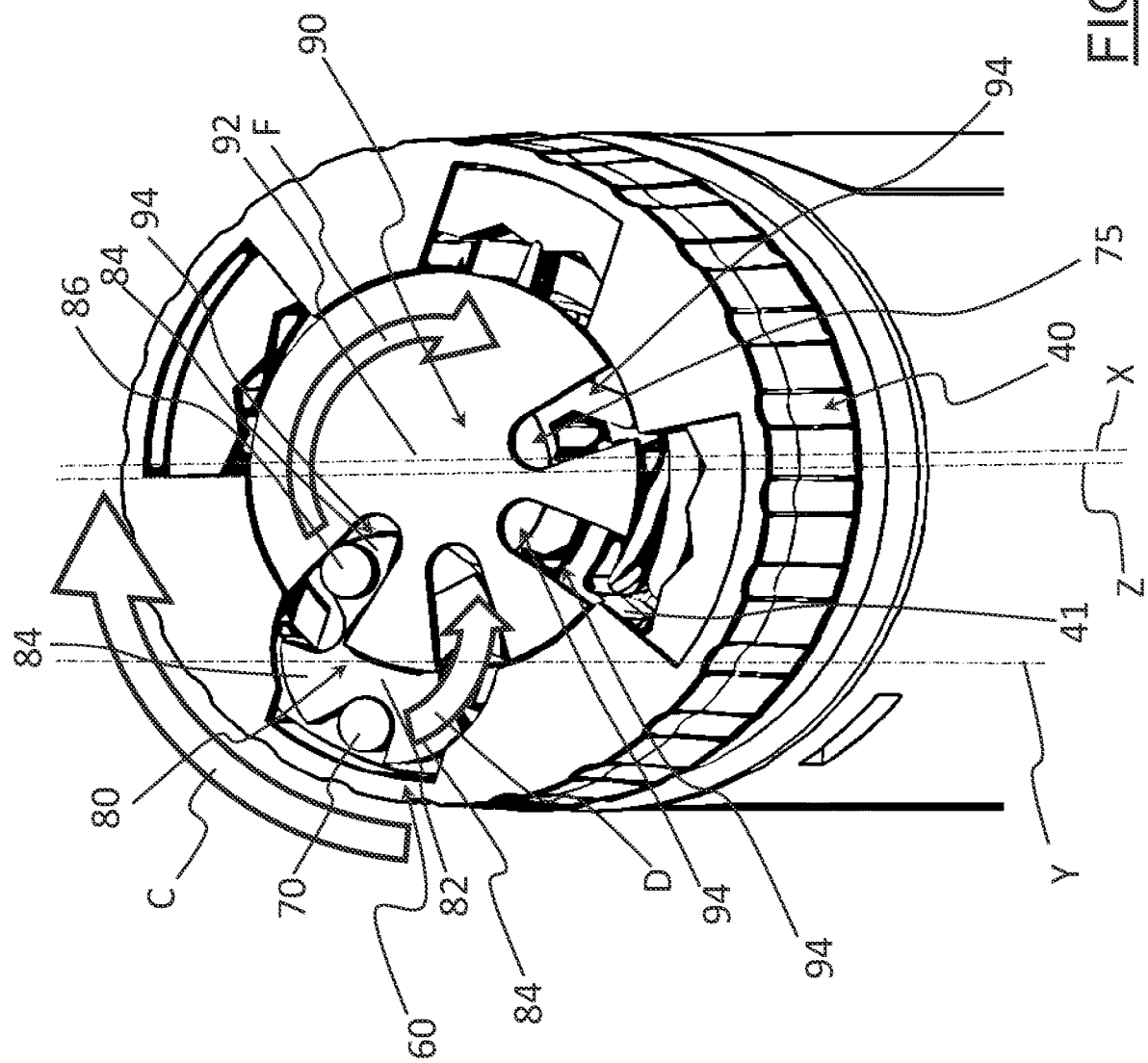
FIG. 9 is a schematic perspective view of a proximal part of the injection device of FIG. 3, showing a first transversal section of a second embodiment of a last dose setting device in a first configuration thereof.
Figure 10:
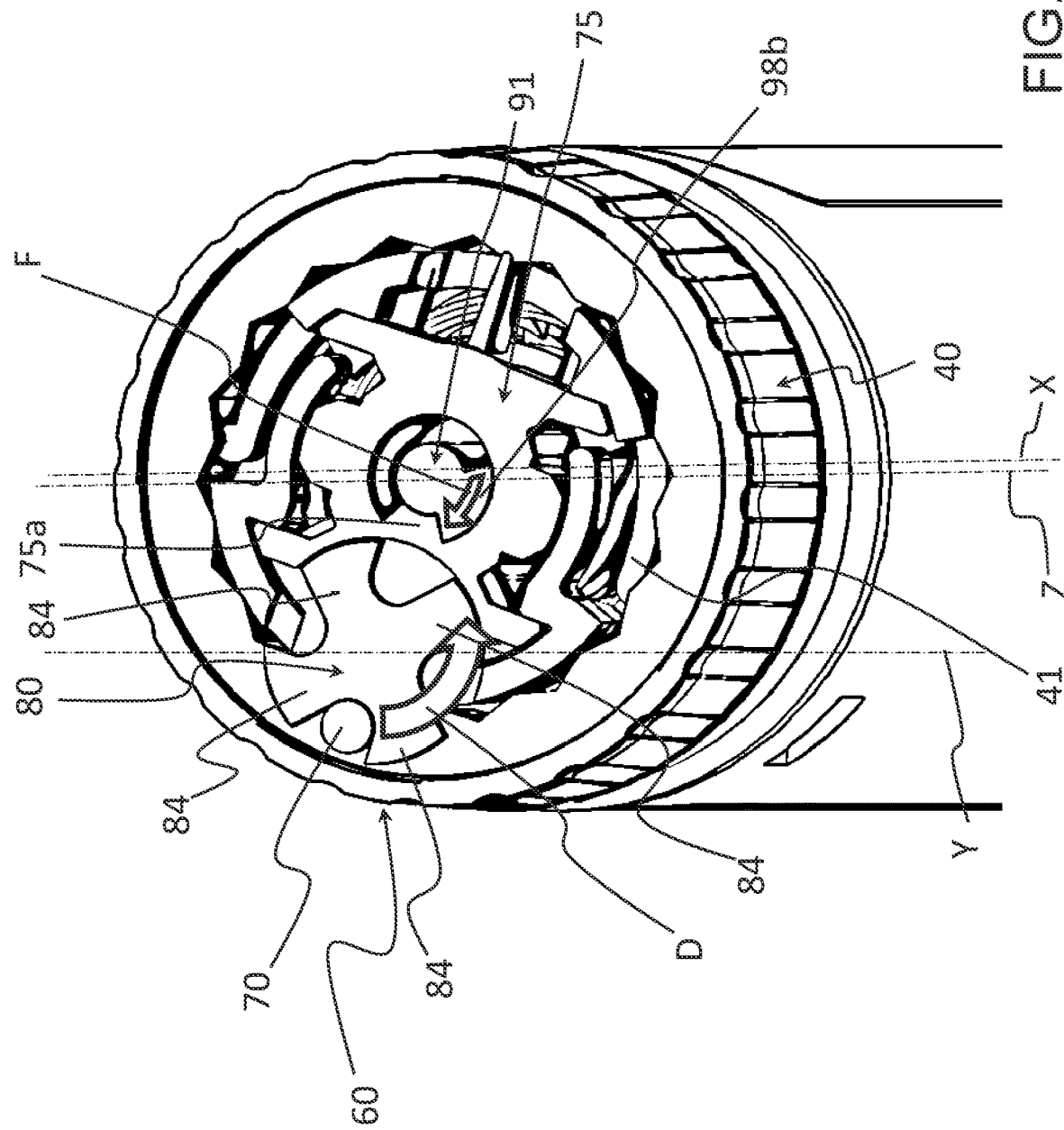
FIG. 10 is a schematic perspective view of the proximal part of FIG. 9, showing a second transversal section of the last dose setting device of FIG. 9 in a final configuration thereof, the second transversal section being less proximal than the first transversal section.

FIGS. 9 and 10 show a second embodiment of a last dose setting device 60 arranged within the hollow body 41 of the knob 40. Components which are structurally or functionally analogous to those of the last dose setting device 60 of FIGS. 4-8 are indicated by the same numerical references. These components will not be described again.

The last dose setting device 60 of FIGS. 9 and 10 comprises, in addition to the main drive pin 70, the drive wheel 80 and the driven wheel 90, an abutment element 98b which is integrally formed with the rotation pin 91 of the driven wheel 90 and a stop member 75 (FIG. 10).

In this specific case the driven wheel 90 has four slots 94.

The abutment element 98b radially protrudes from the rotation pin 91.

The stop member 75 abuts against the abutment element 98b to prevent the rotation of the driven wheel 90 about the rotation axis Z when the knob 40 has made the predetermined number of full and/or partial rotations about the longitudinal axis X and the drive wheel 80 abuts against the main drive pin 70.

FIG. 9 shows a configuration of the last dose setting device 60 which occurs during the drug dose setting.

In such a configuration a first arm 84 of the drive wheel 80 abuts against the main drive pin 70 and the auxiliary drive pin 86 is housed within a first slot 94, so that a rotation about the longitudinal axis X in the clockwise direction of the knob 40 (arrow C) causes the drive wheel 80 to be driven in rotation by the main drive pin 70 in the counter-clockwise direction about the rotation axis Y (arrow D) by 90°. The rotation about the rotation axis Y of the drive wheel 80 causes the rotation about the rotation axis Y of the auxiliary drive pin 86, which drives in rotation the driven wheel 90 in the clockwise direction (arrow F) about the rotation axis Z, so that a relative rotation of the driven wheel 90 with respect to the drive wheel 80 is performed. Such a relative rotation causes the exit of the auxiliary drive pin 86 from the first slot 94.

Starting from the configuration of FIG. 9, after four full rotations of the knob 40, the auxiliary drive pin 86 engages the second slot 94, i.e., the slot 94 adjacent to the first slot 94 in the counter-clockwise direction about the rotation axis Z.

In the same manner, after other four full rotations of the knob 40, the auxiliary drive pin 86 engages the third slot 94, and after other four full rotations of the knob 40 the auxiliary drive pin 86 engages the fourth slot 94.

FIG. 10 shows a configuration of the last dose setting device 60 wherein the auxiliary drive pin 86 of the drive wheel 80 engages the fourth slot 94 and the abutment element 98b of the driven wheel 90 abuts against a portion 75a of the stop member 75.

The abutment element 98b reaches the position of FIG. 10 when the knob 40 has made a predetermined number of full and/or partial rotations about the longitudinal axis X correlated to the predetermined drug volume to be dispensed. In the configuration of FIG. 10 any further rotation of the driven wheel 90 and of the drive wheel 80 about the longitudinal axis X is prevented.

In particular, FIG. 10 shows that the arm 84 of the drive wheel 80 is abutting against the main drive pin 70, so that the drive wheel 80 tends to be driven in rotation by the main drive pin 70 in the counter-clockwise direction about the rotation axis Y according to arrow D. Accordingly, the auxiliary drive pin 86 tends to drive in rotation the driven wheel 90 in the clockwise direction about the rotation axis Z according to arrow F. However, the driven wheel 90 cannot perform such a rotation because of the abutment between the abutment element 98b and the portion 75a of the stop member 75.

Should the user try to set a dose greater than the one currently and actually available in the cartridge 17, the abutment element 98b prevents further relative rotation between the driven wheel 90 and the drive wheel 80, thus preventing the user to set such a dose.

Figure 11:
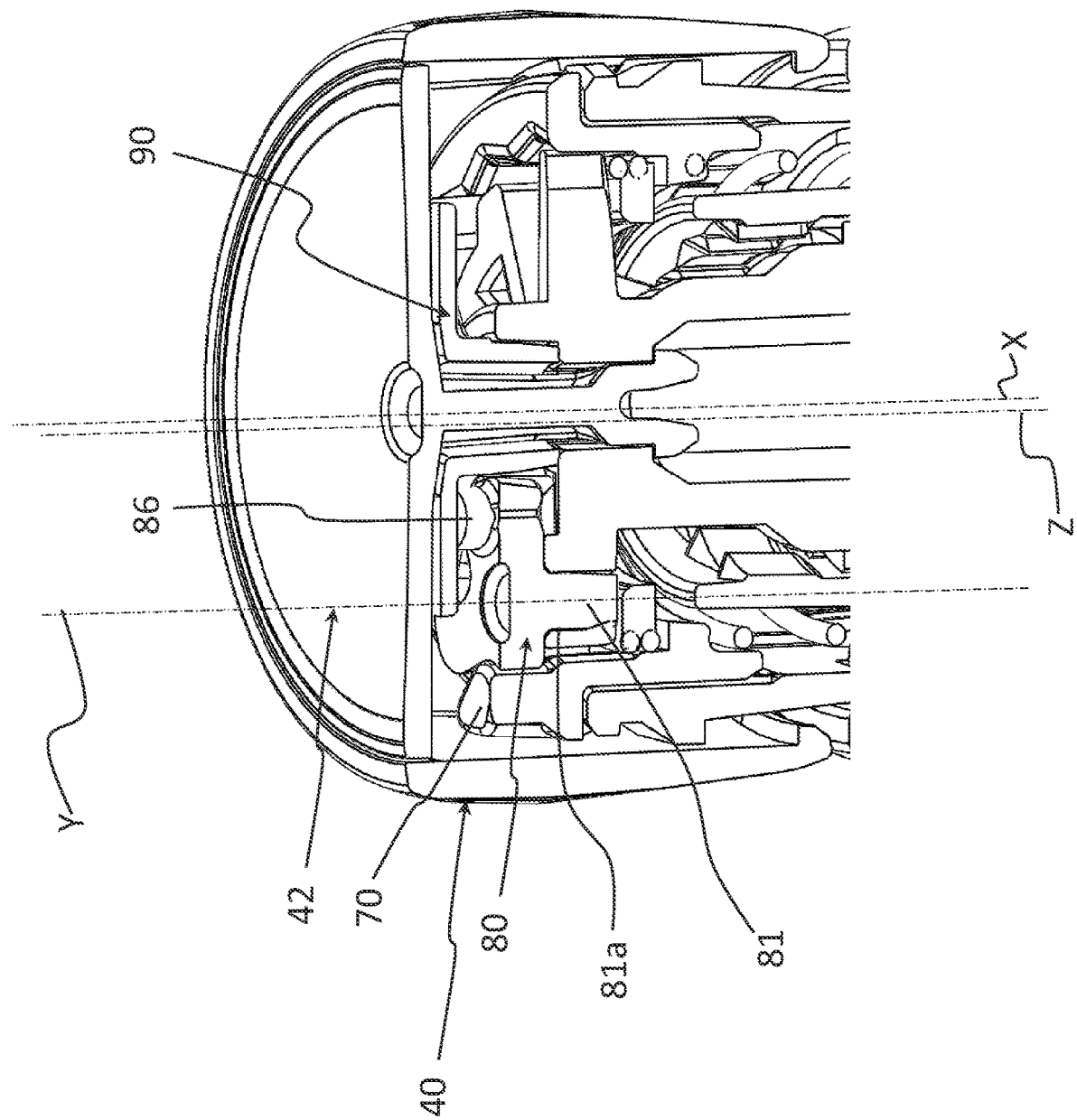
FIG. 11 is a schematic perspective view of a proximal part of the injection device of FIG. 3, showing a longitudinal section of a third embodiment of a last dose setting device in a first configuration thereof.
Figure 12:
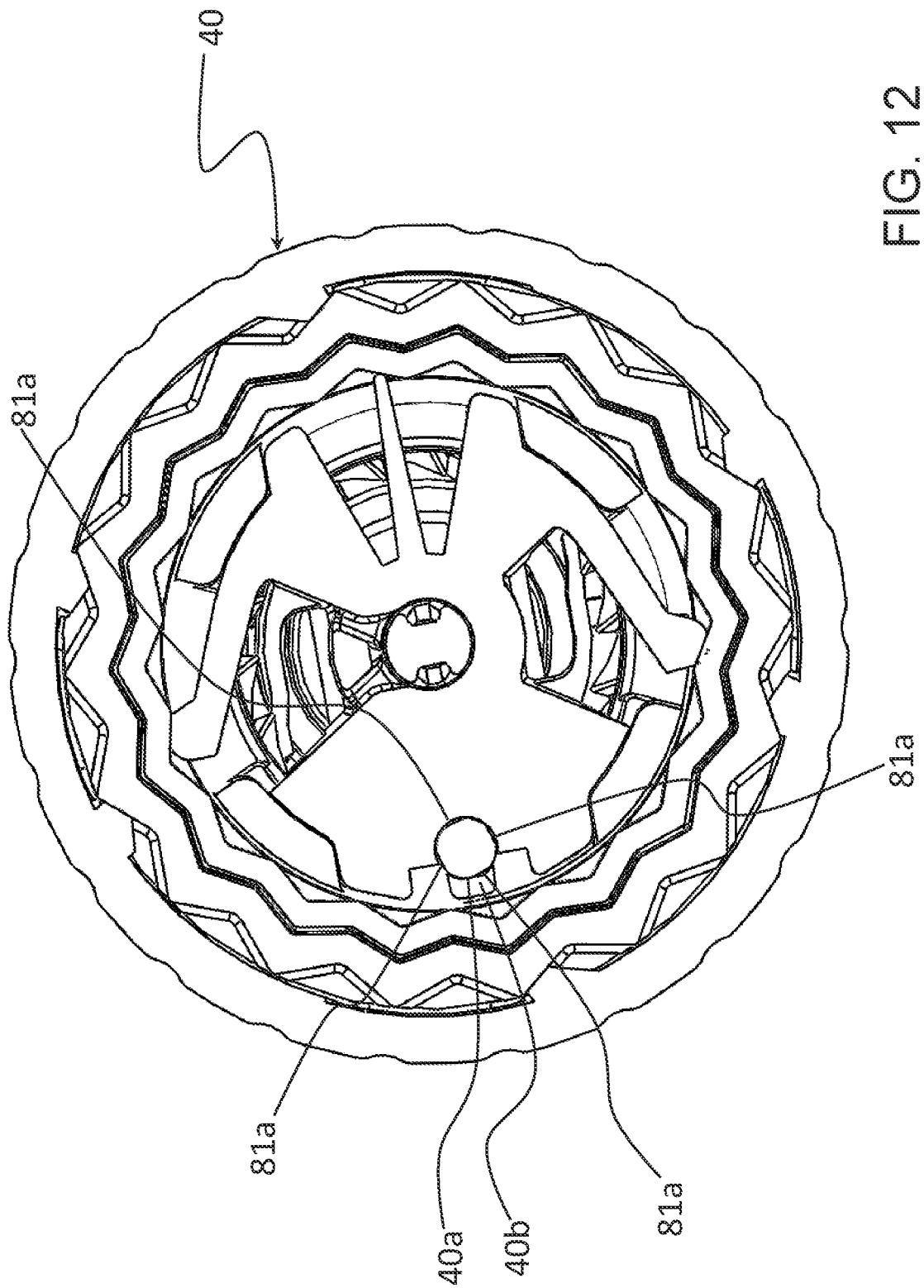
FIG. 12 is a schematic transversal section of the proximal part of the injection device of FIG. 11.

FIGS. 11 and 12 show a third embodiment of a last dose setting device 60 arranged within the hollow body 41 of the knob 40. Components which are structurally or functionally analogous to those of the last dose setting device 60 of FIGS. 4-8 are indicated by the same numerical references. These components will not be described again.

The last dose setting device 60 of FIGS. 11 and 12 differs from the last dose setting device 60 of FIGS. 4-8 in those members which are specifically provided to prevent the rotation of the drive wheel 80 about the first rotation axis Y when the drive wheel 80 rotates about the longitudinal axis X and does not engage the main drive pin 70.

Indeed, in the last dose setting device 60 of FIGS. 11 and 12 the circumferential rail 76 of the last dose setting device 60 of FIGS. 4-8 is not provided.

Instead, the rotation pin 81 of the drive wheel 80 of FIGS. 11 and 12 is not entirely cylindrically-shaped, but it has at least a portion having a "less than round" cross-section profile.

In particular, the outer surface of the rotation pin 81 has a predetermined number of plane faces 81a which extend parallel to the rotation axis Y.

The number of the plane faces 81a and their positions about the rotation axis Y are correlated to the number of arms 84 of the drive wheel 80 and to the angle of rotation performed by the drive wheel 80 about the rotation axis Y every full rotation of the knob 40 about the longitudinal axis X. In the embodiment herein shown, as the arms 84 are four and are equally spaced apart from each other about the rotation axis Y by an angle of 90° (that is the first angle is 90°), the plane faces 81a are four and they are equally spaced apart from each other about the rotation axis Y by an angle of 90°.

The plane faces 81a periodically matches a similar plane face 40a provided in an insert 40b which moves integrally with the knob 40.

In an embodiment not shown, the plane face 40a is integrally formed with the knob 40.

A plane face 81a is coupled with the plane face 40a so as to prevent any relative rotation of the rotation pin 81 of the drive wheel 80 with respect to the insert 40b when the drive wheel 80 does not engage with the main drive pin 70. When an arm 84 of the drive wheel 80 engage with the main drive pin 70, the drive wheel 80 rotates about the rotation axis Y and the plane face 81a is decoupled from the plane face 40a. A rotation of 90° of the rotation pin 81 with respect to the insert 40b occurs. After such a relative rotation a new configuration is reached wherein another plane face 81a is coupled with the plane face 40a of the insert 40b.

FIG. 13 shows a fourth embodiment of a last dose setting device 60 arranged within the hollow body 41 of the knob 40. Components which are structurally or functionally analogous to those of the last dose setting device 60 of FIGS. 4-8 are indicated by the same numerical references. These components will not be described again.

The last dose setting device 60 of FIG. 13 differs from the last dose setting device 60 of FIGS. 4-8 in those members which are specifically provided to prevent the rotation of the driven wheel 90 about the rotation axis Z when the driven wheel 90 rotates about the longitudinal axis X and does not engage the auxiliary drive pin 86.

Indeed, in the last dose setting device 60 of FIG. 13 the drive wheel 80 is not provided with the D-shaped protrusion 83 and the driven wheel 90 of the last dose setting device 60 of FIG. 13 is not provided with the recesses 96.

Instead, the rotation pin 91 of the driven wheel 90 of FIG. 13 comprises a plurality of notches 91a formed on the outer surface thereof and extending parallel to the rotation axis Z.

The notches 91 are coupled to a ratchet pin 40c which rotates integrally with the knob 40.

The ratchet pin 40c engages a notch 91a during rotation of the knob 40 about the longitudinal axis X, so as to drive in rotation the driven wheel 90 too. Each time the auxiliary drive pin 86 of the drive wheel 80 engages a slot 94 in the driven wheel 90 and drives in rotation the latter about the rotation axis Z, the ratchet pin 40c is forced out of the notch 91a and a rotation of the driven wheel 90 with respect to the ratchet pin 40c occurs. After such a rotation the ratchet pin 40c engages with another notch 91a.

Of course, those skilled in the art can bring numerous modifications and changes to the invention described above in order to satisfy specific and contingent requirements, all of which are within the scope of protection defined by the following claims.

The invention claimed is:

1. A drug injection device comprising:
a drug container extending along a longitudinal axis and configured to include a predetermined drug volume;
a dose setting mechanism configured to set a drug dose to be delivered out of the drug container;
a dose delivery mechanism configured to deliver the drug dose set by the dose setting mechanism;
a knob configured to rotate about said longitudinal axis during a drug dose setting;
a last dose setting device configured to prevent a user to set a drug dose greater than the drug volume remaining in the drug container after at least one previous drug dose delivery, wherein the last dose setting device comprises:
a main drive pin which is stationary or is configured to move along a first direction of said longitudinal axis without rotating about said longitudinal axis during the drug dose setting and to move along a second direction opposite to said first direction without rotating about said longitudinal axis during a drug dose delivery;
a drive wheel having a first rotation axis parallel to said longitudinal axis and configured to be driven in rotation about the longitudinal axis by the knob, and to be periodically driven in rotation about the first rotation axis by the main drive pin, during the drug dose setting;
a driven wheel having a second rotation axis parallel or coaxial to said longitudinal axis and configured to be periodically driven in rotation about the second rotation axis by the drive wheel;
an abutment element fixedly coupled to, or integrally formed with, the driven wheel and configured to prevent the rotation of the drive wheel about the longitudinal axis when the knob has made a predetermined number of full and/or partial rotations about the longitudinal axis correlated to the predetermined drug volume;
wherein when the knob has made said predetermined number of full and/or partial rotations about the longitudinal axis, said drive wheel abuts against said main drive pin and said abutment element, or wherein the last dose setting device further includes a stop member configured to abut against said abutment element and to prevent the rotation of the driven wheen about the second rotation axis when the knob has made said predetermined number of full and/or partial rotations about the longitudinal axis and said drive wheel abuts against said main drive pin.

2. The drug injection device according to claim 1, wherein the knob is configured to move along said first direction rotating about said longitudinal axis during the drug dose setting and to move along said second direction without rotating about said longitudinal axis during the drug dose delivery.

3. The drug injection device according to claim 1, wherein before setting a first drug dose the main drive pin, the drive wheel and the driven wheel are arranged with respect to each other so that when the knob has made the predetermined number of full and/or partial rotations about the longitudinal axis the predetermined drug volume is delivered.

4. The drug injection device according to claim 1, wherein the knob comprises a hollow body and wherein said drive wheel, said driven wheel and said main drive pin are housed in said hollow body.

5. The drug injection device according to claim 1, wherein said main drive pin drives in rotation the drive wheel about the first rotation axis by a predetermined first angle every full rotation of the knob about the longitudinal axis and the drive wheel drives in rotation the driven wheel about the second rotation axis by a predetermined second angle every full rotation of the drive wheel about the first rotation axis.

6. The drug injection device according to claim 1, wherein said drive wheel comprises a first central body and a predetermined number of arms extending substantially radially from the first central body, wherein at least one of the arms has an auxiliary drive pin extending substantially parallel to said longitudinal axis and configured to periodically engage with said driven wheel during rotation of the drive wheel about the first rotation axis.

7. The drug injection device according to claim 6, wherein said driven wheel comprises a second central body and a predetermined number of slots extending substantially radially from the second central body and configured to receive said auxiliary drive pin during rotation of the drive wheel about the first rotation axis.

8. The drug injection device according to claim 1, wherein the last dose setting device comprises first members configured to prevent the rotation of the drive wheel about the first rotation axis when the drive wheel rotates about the longitudinal axis and does not engage with the main drive pin.

9. The drug injection device according to claim 6, wherein the last dose setting device comprises second members configured to prevent the rotation of the driven wheel about the second rotation axis when the driven wheel rotates about the longitudinal axis and does not engage with the auxiliary drive pin.

10. The drug injection device according to claim 1, wherein said main drive pin is provided on a sleeve configured to slide along said longitudinal axis integral with the knob or on a ring element fixedly coupled to said sleeve.

11. The drug injection device according to claim 7, wherein the last dose setting device comprises second members configured to prevent the rotation of the driven wheel about the second rotation axis when the driven wheel rotates about the longitudinal axis and does not engage with the auxiliary drive pin.

12. The drug injection device according to claim 6, wherein the last dose setting device comprises first members configured to prevent the rotation of the drive wheel about the first rotation axis when the drive wheel rotates about the longitudinal axis and does not engage with the main drive pin; and wherein the last dose setting device comprises second members configured to prevent the rotation of the driven wheel about the second rotation axis when the driven wheel rotates about the longitudinal axis and does not engage with the auxiliary drive pin.

13. The drug injection device according to claim 7, wherein the last dose setting device comprises first members configured to prevent the rotation of the drive wheel about the first rotation axis when the drive wheel rotates about the longitudinal axis and does not engage with the main drive pin; and wherein the last dose setting device comprises second members configured to prevent the rotation of the driven wheel about the second rotation axis when the driven wheel rotates about the longitudinal axis and does not engage with the auxiliary drive pin.

\* \* \* \* \*